United States Patent [19]

Massey et al.

[11] Patent Number: 4,839,341
[45] Date of Patent: Jun. 13, 1989

[54] STABILIZED INSULIN FORMULATIONS

[75] Inventors: Eddie H. Massey; Theodore A. Sheliga, both of Indianapolis, Ind.

[73] Assignee: Eli Lilly and Company, Indianapolis, Ind.

[21] Appl. No.: 120,443

[22] Filed: Nov. 13, 1987

Related U.S. Application Data

[63] Continuation of Ser. No. 8,493, Jan. 29, 1987, abandoned, which is a continuation of Ser. No. 749,371, Jun. 27, 1985, abandoned, which is a continuation-in-part of Ser. No. 614,355, May 29, 1984, abandoned.

[51] Int. Cl.$^4$ .............................................. A61K 37/26
[52] U.S. Cl. .......................................... 514/4; 514/3; 514/494
[58] Field of Search ................................ 514/3, 4, 494

[56] References Cited

U.S. PATENT DOCUMENTS 4,129,560 12/1978 Zoltobrocki ........................ 530/308

FOREIGN PATENT DOCUMENTS 1146069 5/1983 Canada .
83/00288 2/1983 Denmark .

OTHER PUBLICATIONS

Touitou et al., *International Journal of Parmaceutics*, 15, 13-24 (1983).
Touitou et al., *J. Pharm. Pharmac.*, 30, 662-3 (1978).
Chawla et al., *Diabetes*, 34, 420-424 (1985).
*The Merck Index*, 9th ed. Merck & Co Inc., Rahway, N.J., 1976, Entry No. 7342, p. 983.
USAN and the USP Dictionary of Drug Names, Ed. by Mary C. Griffiths, U.S. Pharmacopeil Convention, Inc. Rockville, Md., p. 260, from Jun. 15, 1961, Through Jun. 15, 1979.
Wu et al., *Biochimics et Biophysica Acta*, 667, 285-293 (1981).
Swim, H. E. and Parker, R. F. Effect of Pluronic F68 on Growth of Fibroblasta in Suspension on Rotary Shaker. *Proc. Soc. Exp. Bio. Med.* 103, 252 (1960).
Lougheed, D., Albisser, A. M., Chow, J. C. and Clement, J. R. Physical Stability of Insulin Formulations. *Diabetes* 32, 424 (1983).
Henry, M., McMullen, J. K., Grant, A. P., Tindall, C. E. A Solution for Insulin Aggregation. *Irish J. Med. Sci.* 230 (1982).
Thurow et al., *Diabetoligia* 27, 212-218 (1984).

Primary Examiner—Delbert R. Phillips
Assistant Examiner—F. T. Moezie
Attorney, Agent, or Firm—William C. Martens; Leroy Whitaker

[57] ABSTRACT

This invention provides an insulin formulation stabilized against aggregation containing a hydroxybenzene and a polyethylene glycol-polypropylene glycol polymer of the formula

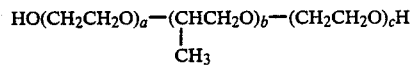

having an average molecular weight of about 8350 and in which the average number of ethyleneoxy units per molecule, designated by the sum of a and c, is about 150, and the average number of propyleneoxy units per molecule, designated as b, is about 30.

12 Claims, No Drawings

STABILIZED INSULIN FORMULATIONS

This application is a continuation of application Ser. No. 07/008,493, filed 1/29/87, which is a continuation of now abandoned application Ser. No. 749,371, filed June 27, 1985; which is a continuation-in-part of application Ser. No. 614,355, filed May 29, 1984, now abandoned.

BACKGROUND OF THE INVENTION

The use of mechanical continuous infusion devices that will deliver insulin to diabetic patients within narrow dose tolerances for periods of one day to several weeks has been investigated extensively and reviewed in the literature [see, for example, Eaton, R. P., *Diabetes Care* 3:253-54, (1980); Prestele, K., Franetzki, M., and Kresse, H., *Diabetes Care* 3:362-68 (1980); Goriya, Y., Bahoric, A., Marliss, E. B., Zinman, B., and Albisser, A. M., *Diabetes* 28:558-64 (1980); Albisser, A. M., Botz, C. K., and Leibel, B. S., *Diabetologia* 16:129-33 (1979); Albisser, A. M., *Proc. IEEE* 67:1308-20 (1979); Santiago, J. V., Clemens, A. H., Clarke, W. L., and Kipins, D. M., *Diabetes* 28:71-84 (1979); A. M. Albisser, *Diabetes Mellitus: Current and Future Therapies* (M. Brownlee, ed.) Garland STPM Press, New York, Vol. 5:245-272, (1981); and Rizza, R. A., Gerich, J. E., Haymond, M. W., Westland, R. E., Hall, L. D., Clemens, A. H., and Service, J. F., *New Engl. J. Med.* 303:1313-18 (1980)]. "Open-loop" ambulatory pumps that deliver insulin by continuous infusion are commercially available, and implanted devices are being studied clinically [see, for example, Schade, D. S., Eaton, R. P., Edwards, W. S., Doberneds, R. C., Spencer, W. I., Carlson, G. A., Bair, R. E., Love, J. T., Urenda, R. S. and Gaona, J. I., *J. Am. Med. Assoc.* 247:1848-53 (1982); and Irsigler, K., Kritz, H., Hagmuller, G., Franetzki, M., Prestele, K., Thurow, H., and Geisen, K., *Diabetes* 30, 1072-75 (1981)]. Insulin delivery by continuous infusion devices carries a number of advantages relative to delivery by periodic bolus injections, the principal of which is that it permits the diabetic patient to maintain a more nearly normal glycemic and metabolic state and, thus, to experience an increased flexibility of lifestyle.

The insulin solution to be delivered by an infusion device is maintained in a reservoir, for example, a syringe, a synthetic polymeric bladder, a metal container, and the like. The reservoir and its associated pumping mechanism can be maintained externally or implanted in the patient. The insulin is delivered from the reservoir via small diameter catheters composed of synthetic polymeric materials.

A major problem encountered in delivering insulin by infusion systems is the tendency of insulin solutions over time to produce insulin aggregates, fibrils, or precipitates [see, for example, Lougheed, W. P., Woulfe-Flanagan, H., Clement, J. R., and Albisser, A. M., *Diabetologia*, 19:1-9 (1980)]. The aggregates and precepitates lead to obstruction of the catheter or pump components and the obstruction, in turn, to the interruption of the flow of insulin to the patient, resulting in poor glycemic control. Many factors have been implicated in the aggregation and precipitation of insulin in solution; however, those factors promoting aggregation and precipitation most likely to be encountered in all types of continuous infusion equipment are:
  (a) elevated temperatures, e.g., 25°-37° C., as opposed to the usual 5° C., storage conditions [Fisher, H. and Porter, P. B., *Pharmaceut. Pharmacol.* 33:203-06 (1980)];
  (b) agitation, potentially caused by body movement or movement of pumping mechanisms [Irsigler, K., and Kritz, H., *Diabetes* 28:196-203 (1980)];
  (c) association with an extended exposure of insulin molecules to hydrophobic surfaces, such as air interfaces and plastic or metal pump components [Weisenfeld et. al., *Diabetes*, 17, 766 (1968); and Browe et al., *Eur. J. Biochem.*, 33, 233 (1973)]; and
  (d) outside stimuli, such as diffusion of $CO_2$ through semi-permeable plastic or rubber components that cause the pH of insulin solutions to drift toward the isoelectric pH (pH 5.4) of insulin, where its solubility is very low [Lougheed et al., supra].

The principal approach for preventing or delaying insulin-related obstructions in infusion devices has been to modify insulin preparations by addition of an "anti-aggregation" stabilizer. Several additives or kinds of additives have been proposed as solutions to the aggregation problem. Among these are:
  (a) sodium bicarbonate;
  (b) acidic insulin solutions [Schade, D. S., et. al. Satellite Symposium to 16th European Association for the Study of Diabetes Meeting, Greece, 22-23 Sept. 1980, P. 107];
  (c) acidic amino acids [Bringer, J., Heldt, A., and Grodsky, M., *Diabetes* 30: 83-85 (1981)];
  (d) non-polar and non-aqueous solvents;
  (e) calcium and magnesium ions [Havelund, Jorgen, and Grange, U.K. Patent Application No. GB2094145A];
  (f) ionic surfactants [Lougheed et al., supra]; and
  (g) non-ionic surfactants [German Patent Application P2959119.5; and Henry, M., McMullen, J. K., Grant, H. P., and Tindall, C. E., *Irish Journal of Medical Science*, 230 (1982)].

Each of the above reagents or classes is perhaps useful under certain well-defined and limited conditions. The deficiency of each as a general class, however, is that it protects insulin from aggregation or precipitation caused by only one or less than all of the several possible mechanisms. It is probable that all factors implicated in the obstruction of insulin infusion systems are operative during actual use of infusion devices, or, if all are not operative in any selected isolated use of an infusion device, all certainly are cumulatively present in the wide range of conditions under which infusion devices are used.

Sodium bicarbonate and acidic anti-aggregation stabilizers, for example, prevent isoelectric precipitation of insulin; they are not, however, effective in protecting insulin from agitation-induced aggregation (denaturation) or temperature-induced fibril formation. Moreover, acidic insulin solutions degrade rapidly.

Ionic and non-ionic surfactants, whether physiologic or synthetic, are recognized to reduce the propensity of insulin to precipitate from solution by mechanical stress or surface interactions [U.S. Pat. 4,120,560; European Patent Application No. 80102252.6]. It has also been reported that a synthetic non-ionic polyethylene-polypropylene glycol surfactant, Pluronic Polyol F-68, is effective in eliminating precipitation of protein from a horse serum-containing medium used in mechanically-shaken tissue culture [Swim et al., *Proc. Soc. Exp. Bio. Med.* 103, 252 (1960)].

The recognized protein-solvation characteristics of surfactants and their potential for maintaining insulin conformation [Wu, C-S. C., and Yang, J. T., *Biochem. Biophys. Acta* 667:285-93 (1981)] makes them recognized as likely candidates as insulin anti-aggregation stabilizers. Notwithstanding this fact, surfactants would not be expected to inhibit aggregation and precipitation caused by other factors, e.g., pH drift.

The present invention defines novel insulin formulations having substantially delayed insulin aggregation or precipitation properties. The insulin formulations of this invention contain a selected polypropylene-polyethylene glycol surfactant in combination with a phenol. The insulin formulations of the invention, containing the selected polypropylene-polyethylene glycol and a hydroxybenzene, exhibit a surprising and unexpectedly high retardation of insulin aggregation. It was further discovered that insulin formulations containing the selected polypropylene-polyethylene glycol but lacking a hydroxybenzene showed only a mild protective effect against insulin aggregation and precipitation, and, moreover, that those formulations containing a hydroxybenzene but none of the selected polypropylene-polyethylene glycol actually hastened insulin aggregation.

SUMMARY OF THE INVENTION

Thus, this invention is directed to an insulin formulation comprising, in a pharmaceutically acceptable aqueous diluent and per each milliliter of formulation, from about 40 U to about 500 U of insulin, from about 1 to about 6 milligrams of a hydroxybenzene, and from about 0.05 to about 10 milligrams of a polyethylene glycol-polypropylene glycol polymer of the formula X-6077A

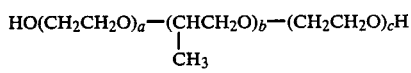

having an average molecular weight of about 8350 and in which the average number of ethyleneoxy units per molecule, designated by the sum of a and c, is about 150, and the average number of propyleneoxy units per molecule, designated as b, is about 30.

DETAILED DESCRIPTION OF THE INVENTION

As noted, this invention is directed to insulin formulations particularly suited for use in infusion device systems. The formulations comprise insulin, a phenol, and a specific polyethylene glycol-polypropylene glycol polymer in a suitable diluent.

The insulin contemplated for use in the formulations of this invention can structurally be that of any species. Preferably, the insulin will have the structure of that produced by humans, cattle, or pigs, and, most preferably, by humans. The source of the insulin is not critical to this invention. Thus, for example, it may be isolated from the pancreas; synthesized by classical chemical synthesis; converted chemically or enzymatically from that of one species to that of another, e.g., pork to human; produced by recombinant DNA methodology; or any other available method.

The insulin may be present in the formulation in varying concentrations ranging from about 40 U/ml. to about 500 U/ml. and, preferably, from about 80 U/ml. to about 100 U/ml., and can be present in the presence or absence of cations such as zinc or sodium. The preferred cation is zinc, and it preferably is present in an amount of from about 0.3% to about 0.7% by weight, based upon the insulin content in the formulation.

Another component of the formulations of this invention is a hydroxybenzene. The hydroxybenzene is present in an amount of from about 1 mg. to about 6 mg. per each ml. of the insulin formulation (about 0.1% to about 0.6% by weight). Preferably, the hydroxybenzene is present in an amount ranging from about 2.5 mg. to about 3 mg. per each ml. of the formulation. Typical hydroxybenzenes are, for example, phenol, m-cresol, o-cresol, p-cresol, o-chlorophenol, m-chlorophenol, p-chlorophenol, o-phenylphenol, ethyl p-hydroxybenzoate, methyl p-hydroxybenzoate, and the like. Preferred hydroxybenzenes are phenol and m-cresol. Moreover, mixtures of hydroxybenzenes may be present in the formulation. For example, the formulation may contain a combination of about 3 mg. m-cresol and about 2 mg. phenol per each ml. of formulation.

Another essential component of the compositions of this invention is the polyethylene glycol-polypropylene glycol copolymer. It is a long chain polymer having an average molecular weight of about 8350 and containing, on the average, about 150 ethyleneoxy moieties and about 30 propyleneoxy moieties. The United States Adopted Name (USAN) for a material having these structural characteristics is Poloxamer 188. One such material is marketed under the tradename Pluronic Polyol F-68 ®, and is highly preferred for use as the copolymer component of the formulations of this invention. The copolymer is present in the formulations in an amount ranging from about 0.05 mg. to about 10 mg. per milliliter of the final composition (about 0.005% to about 1% by weight). Preferably, Poloxamer 188 is present in an amount of at least about 0.2 mg. per milliliter of the final composition.

Although not an essential part of the compositions of this invention, the compositions preferably also contain a suitable buffer, such as TRIS (2-amino-2-hydroxymethyl-1,3-propanediol), glycinamide, leucinamide, phosphate ion bicarbonate ion, and the like. The preferred buffers are TRIS and glycinamide. The presence of such buffers carry the added benefit of assisting the compositions of this invention in retarding insulin aggregation and precipitation caused by pH drift. In general, when present, the selected buffer will be present in an amount ranging from about 0.2% to about 0.8% by weight of the final composition.

If desired, the compositions of this invention may also contain a tonicity agent. Typical such agents are glycerin, sodium chloride, and the like, and, when present, are present in an amount ranging from about 0.5% to about 2.0% by weight, based upon the final composition.

The insulin formulations of this invention can be prepared using any of a number of recognized methods. Preferably, however, the formulations are prepared by (a) suspending zinc insulin, for example, purified pork insulin, human insulin, or the like, in an aqueous solution containing (i) the selected amount of the hydroxybenzene or mixture of hydroxybenzenes, (ii) a non-ionic osmotic pressure regulating agent, for example, glycerol, in an amount that will render the final solution isotonic, and (iii) a polypropylene-polyethylene glycol polymerisate, for example, Pluronic Polyol F-68 ®; (b) adding dilute aqueous acid, preferably hydrochloric acid, in an amount sufficient to maintain the pH of the mixture from about 3.2 to about 3.8 until all of the suspended insulin dissolves; (c) adding to the thus-formed acidic solution a solution containing the desired buffering agent, for example, TRIS or glycinamide, which has been adjusted to a pH that will produce a final solution having a pH of from about 7.0 to about 7.8; and (d) diluting the thus-formed solution to the desired insulin concentration and final pH using water and dilute acid or dilute base, as necessary.

The improved stability against insulin aggregation available from the formulations of this invention is demonstrated using an agitation test method. A sample (1 ml.) of the formulation is pipetted into each of six type I (5 ml.) glass ampoules. The ampoules are sealed using a gas/oxygen flame. Four of the six ampoules are secured horizontally to an Eberbach Model 5850 reciprocating shaker set at 250 oscillations per minute with a one inch stroke in a 37° C. incubator. The remaining two ampoules are placed in the incubator as stationary samples. In addition, an equal number of ampoules containing a control solution, usually a "commercial" type regular insulin formulation, are included.

For example, a suitable control for use in testing the formulations of this invention is as follows:

| Insulin | 100 U/ml. |
| Glycerin | 1.60% |
| m-Cresol | 0.3% |
| pH | 7.40 |

The ampoules are observed periodically for visual signs of aggregation as evidenced by the appearance of haze or precipitates. A Stabilization Index (SI) is determined, which is the ratio of the average time elapsed before the appearance of the first signs of aggregation of the experimental formulation to that of the control formulation. Using this test system, the following results were obtained for human insulin (Table 1) and porcine insulin (Table 2).

TABLE 1

Stabilization of Human Insulin Against Aggregation

| Insulin, U/ml. | m-Cresol, Wt. Percent | Poloxamer 188, Wt. Percent | Buffer, Wt. Percent | Tonicity Agent, Wt. Percent | Phenol, Wt. Percent | Stabilization Index, SI[1] |
|---|---|---|---|---|---|---|
| 100 | — | — | — | Glycerin, 1.6 | — | 2–4 |
| 100 | 0.3 | — | — | Glycerin, 1.6 | — | 1 |
| 100 | — | 0.02 | Glycinamide, 0.22 | Glycerin, 1.6 | 0.3 | 12–>168[2] |
| 100 | 0.25 | 1.0 | TRIS, 0.4 | Glycerin, 1.6 | — | >168[2] |
| 100 | — | 0.02 | — | Glycerin, 1.6 | — | 5–6 |
| 100 | 0.25 | 0.05 | TRIS, 0.4 | Glycerin, 1.6 | — | 28–60 |

[1]SI of 1 = 4 hours.
[2]Experiment terminated at 28 days.

TABLE 2

Stabilization of Porcine Insulin Against Aggregation

| Insulin, U/ml. | m-Cresol, Wt. Percent | Poloxamer 188, Wt. Percent | Buffer, Wt. Percent | Tonicity Agent, Wt. Percent | Phenol, Wt. Percent | Stabilization Index, SI[1] |
|---|---|---|---|---|---|---|
| 100 | 0.3 | — | — | Glycerin, 1.6 | — | 1 |
| 100 | — | — | — | Glycerin, 1.6 | 0.2 | 1 |
| 100 | — | 0.02 | — | Glycerin, 1.6 | — | 2 |
| 100 | — | — | TRIS, 0.4 | Glycerin, 1.6 | 0.3 | 3–5 |
| 100 | — | 0.02 | — | Glycerin, 1.6 | 0.3 | 2–9 |
| 100 | 0.3 | 0.02 | — | Glycerin, 1.6 | — | >28[2] |
| 40 | 0.3 | 0.02 | — | Glycerin, 1.6 | — | 21–>28[2] |
| 500 | 0.3 | 0.02 | — | Glycerin, 1.6 | — | >28[2] |

[1]SI of 1 = 24 hours.
[2]Experiment terminated at 28 days.

Another series of tests was run under milder agitation conditions. In this method, a sample (1 ml.) of the formulation is pipetted into each of twelve type I (2 ml.) glass vials. The vials are stoppered with a teflon-faced stopper and capped. The vials are secured horizontally to an Eberbach Model 5850 reciprocating shaker set at 100 oscillations per minute with a one inch stroke in a 37° C. incubator. In addition, an equal number of vials containing a control solution are included.

The vials are observed periodically for visual signs of aggregation as evidenced by the appearance of haze or precipitates. Using this test system, the evidence tends to suggest that the presence of a hydroxybenzene in an insulin formulation in the absence of the poly-propylene-polyethylene glycol polymerisate present in the formulations of the present invention in fact accelerates insulin aggregation. In contrast, and quite surprisingly, a combination of both a hydroxybenzene and the poly-propylene-polyethylene glycol polymerisate in the insulin formulation greatly retards insulin aggregation well beyond that available from the polypropylene-polyethylene glycol polymerisate alone. The tendency of the presence of a hydroxybenzene accelerate insulin aggregation, at least with human and bovine insulin, is demonstrated by the date in Tables 3, 4, and 5. Tables 6, 7, 8, 9, 10, and 11 summarize studies with human, procine, and bovine insulin, each containing Poloxamer 188 in the presence and absence of phenol or m-Cresol. The advantages of the presence of both Poloxamer 188 and a hydroxybenzene in terms of retardation of insulin aggregation are in every case quite distinctive.

TABLE 3
Shaker Test - Human Insulin (Without Poloxamer 188)

| Insulin, 100 U/ml[a] Lot No. | m-Cresol, wt % | Phenol wt % | Days to Aggregation Range | Mean |
|---|---|---|---|---|
| 237JK4 | — | — | 2–3 | 2.9 |
| " | 0.25 | — | 1–2 | 1.7 |
| " | — | 0.25 | 1 | 1 |
| 568JK4 | — | — | 2–3 | 2.9 |
| " | 0.25 | — | 2–3 | 2.8 |
| " | — | 0.25 | 1–2 | 1.2 |
| 569JK4 | — | — | 3–7 | 3.8 |
| " | 0.25 | — | 1–2 | 1.1 |
| " | — | 0.25 | 2 | 2 |

[a]Formulation contains 1.7% by weight glycerin.

TABLE 4
Shaker Test - Porcine Insulin (Without Poloxamer 188)

| Insulin, 100 U/ml[a] Lot No. | m-Cresol, wt % | Phenol wt % | Days to Aggregation Range | Mean |
|---|---|---|---|---|
| 8DA29 | — | — | 7 | 7 |
| " | 0.25 | — | 16 | 16 |
| " | — | 0.25 | 16 | 16 |
| 8DS96 | — | — | 3 | 3 |
| " | 0.25 | — | 7 | 7 |
| " | — | 0.25 | 7 | 7 |

[a]Formulation contains 1.7% by weight glycerin.

TABLE 5
Shaker Test - Bovine Insulin (Without Poloxamer 188)

| Insulin, 100 U/ml[a] Lot No. | m-Cresol, wt % | Phenol wt % | Days to Aggregation Range | Mean |
|---|---|---|---|---|
| 7NH27 | — | — | 4–7 | 6.2 |
| " | 0.25 | — | 2–3 | 2.9 |
| " | — | 0.25 | 3–7 | 5 |

[a]Formulation contains 1.7% by weight glycerin.

TABLE 6
Shaker Test - Human Insulin (Poloxamer 188 and m-Cresol)

| Insulin, 100 U/ml[a] Lot No. | m-Cresol, wt % | Tris, wt % | Poloxamer 188, wt % | Days to Aggregation Range | Mean |
|---|---|---|---|---|---|
| 237JK4 | 0.25 | — | — | 2 | 2 |
| " | 0.25 | 0.4 | — | 2 | 2 |
| " | — | 0.4 | 0.02 | 8–20 | 14.1 |
| " | 0.25 | 0.4 | 0.02 | 90[b] | 90[b] |
| 568JK4 | 0.25 | — | — | 1 | 1 |
| " | 0.25 | 0.4 | — | 1 | 1 |
| " | — | 0.4 | 0.02 | 3–9 | 7.4 |
| " | 0.25 | 0.4 | 0.02 | 90[b] | 90[b] |
| 569JK4 | 0.25 | — | — | 1 | 1 |
| " | 0.25 | 0.4 | — | 1 | 1 |
| " | — | 0.4 | 0.02 | 3–8 | 6.7 |
| " | 0.25 | 0.4 | 0.02 | 90[b] | 90[b] |

[a]Formulation contains 1.7% weight glycerin.
[b]Test terminated at 90 days without aggregation.

TABLE 7
Shaker Test - Human Insulin (Poloxamer 188 and Phenol)

| Insulin 100 U/ml[a] Lot No. | Phenol, wt % | Tris, wt % | Poloxamer 188, wt % | Days to Aggregation Range | Mean |
|---|---|---|---|---|---|
| 237JK4 | 0.25 | — | — | 5 | 5 |
| " | 0.25 | 0.4 | — | 6–13 | 11.2 |
| " | — | 0.4 | 0.02 | 8–20 | 14.1 |
| " | 0.25 | 0.4 | 0.02 | 78–90[b] | 89 |
| 568JK4 | 0.25 | — | — | 1 | 1 |
| " | 0.25 | 0.4 | — | 3 | 3 |
| " | — | 0.4 | 0.02 | 3–9 | 7.4 |
| " | 0.25 | 0.4 | 0.02 | 90[b] | 90[b] |
| 569JK4 | 0.25 | — | — | 1 | 1 |
| " | 0.25 | 0.4 | — | 7 | 7 |
| " | — | 0.4 | 0.02 | 3–8 | 6.7 |
| " | 0.25 | 0.4 | 0.02 | 90[b] | 90[b] |

[a]Formulation contains 1.7% by weight glycerin.
[b]Test terminated at 90 days without aggregation.

TABLE 8
Shaker Test - Porcine Insulin (Poloxamer 188 and m-Cresol)

| Insulin, 100 U/ml[a] Lot No. | m-Cresol, wt % | Tris, wt % | Poloxamer 188, wt % | Days to Aggregation Range | Mean |
|---|---|---|---|---|---|
| 8DA29 | 0.25 | — | — | 2 | 2 |
| " | 0.25 | 0.4 | — | 2 | 2 |
| " | — | 0.4 | 0.02 | 2–12 | 10.3 |
| " | 0.25 | 0.4 | 0.02 | 90[b] | 90[b] |
| 8DS96 | 0.25 | — | — | 2–5 | 4.5 |
| " | 0.25 | 0.4 | — | 2–5 | 3.5 |
| " | — | 0.4 | 0.02 | 2–6 | 4.2 |
| " | 0.25 | 0.4 | 0.02 | 90[b] | 90[b] |

[a]Formulation contains 1.7% by weight glycerin.
[b]Test terminated at 90 days without aggregation.

TABLE 9
Shaker Test - Porcine Insulin (Poloxamer 188 and Phenol)

| Insulin, 100 U/ml[a] Lot No. | Phenol wt % | Tris, wt % | Poloxamer 188, wt % | Days to Aggregation Range | Mean |
|---|---|---|---|---|---|
| 8DA29 | 0.25 | — | — | 2 | 2 |
| " | 0.25 | 0.4 | — | 2 | 2 |
| " | — | 0.4 | 0.02 | 2–12 | 10.3 |
| " | 0.25 | 0.4 | 0.02 | 90[b] | 90[b] |
| 8DS96 | 0.25 | — | — | 5–6 | 5.2 |
| " | 0.25 | 0.4 | — | 2–6 | 4.8 |
| " | — | 0.4 | 0.02 | 2–6 | 4.2 |
| " | 0.25 | 0.4 | 0.02 | 90[b] | 90[b] |

[a]Formulation contains 1.7% by weight glycerin.
[b]terminated at 90 days without aggregation.

TABLE 10
Shaker Test - Bovine Insulin (Poloxamer 188 and m-Cresol)

| Insulin, 100 U/ml[a] Lot No. | m-Cresol, wt % | Tris, wt % | Poloxamer 188, wt % | Days to Aggregation Range | Mean |
|---|---|---|---|---|---|
| 7NH27 | 0.25 | — | — | 2 | 2 |
| " | 0.25 | 0.4 | — | 2 | 2 |
| " | — | 0.4 | 0.02 | 1 | 1 |

TABLE 10-continued

Shaker Test - Bovine Insulin (Poloxamer 188 and m-Cresol)

| Insulin, 100 U/ml[a] Lot No. | m-Cresol, wt % | Tris, wt % | Poloxamer 188, wt % | Days to Aggregation Range | Mean |
|---|---|---|---|---|---|
| " | 0.25 | 0.4 | 0.02 | 40–90[b] | 77.8 |

[a]Formulation contains 1.7% by weight glycerin.
[b]Test terminated at 90 days without aggregation.

TABLE 11

Shaker Test - Bovine Insulin (Poloxamer 188 and Phenol)

| Insulin, 100 U/ml[a] Lot No. | m-Cresol, wt % | Tris, wt % | Poloxamer 188, wt % | Days to Aggregation Range | Mean |
|---|---|---|---|---|---|
| 7NH27 | 0.25 | — | — | 2 | 2 |
| 7NH27 | 0.25 | 0.4 | — | 2 | 2 |
| 7NH27 | — | 0.4 | 0.02 | 1 | 1 |
| 7NH27[c] | 0.25 | 0.4 | 0.02 | 5–90[b] | 48.1 |
| 7NH27[c] | 0.25 | 0.4 | 0.02 | 13–90[b] | 77.4 |

[a]Formulation contains 1.7% by weight glycerin.
[b]Test terminated at 90 days without aggregation.
[c]Run twice.

We claim:

1. An insulin formulation comprising, in a pharmaceutically acceptable aqueous diluent and per each milliliter of formulation, from about 40 U to about 500 U of insulin, from about 1 to about 6 milligrams of a hydroxybenzene, and from about 0.05 to about 10 milligrams of a polyethylene glycol-polypropylene glycol polymer of the formula $$HO(CH_2CH_2O)_a-(CHCH_2O)_b-(CH_2CH_2O)_cH$$
$$|$$
$$CH_3$$

having an average molecular weight of about 8350 and in which the average number of ethyleneoxy units per molecule, designated by the sum of a and c, is about 150, and the average number of propyleneoxy units per molecule, designated as b, is about 30.

2. Formulation of claim 1, in which the insulin is human insulin.

3. Formulation of claim 2, in which the human insulin is present in a concentration of from about 80 U/ml. to about 100 U/ml.

4. Formulation of claim 1, in which the hydroxybenzene is m-cresol.

5. Formulation of claim 4, in which the m-cresol is present in an amount of from about 2.5 mg. to about 3 mg. per milliliter.

6. Formulation of claim 5, in which phenol is present in addition to m-cresol.

7. Formulation of claim 1, in which the hydroxybenzene is phenol.

8. Formulation of claim 7, in which phenol is present in an amount of from about 2.5 mg. to about 3 mg. per milliliter.

9. Formulation of claim 1, in which a cation selected from zinc or sodium is present.

10. Formulation of claim 9, in which the cation is zinc.

11. Formulation of claim 1, in which the polyethylene glycol-polypropylene glycol polymer is Poloxamer 188.

12. Formulation of claim 11, in which the poloxamer 188 is present in an amount of at least at about 0.2 mg. per milliliter of the final composition.

* * * * *